United States Patent [19]

Galkin

[11] Patent Number: 5,544,238
[45] Date of Patent: *Aug. 6, 1996

[54] METHOD OF AND APPARATUS FOR STANDARDIZING AND MONITORING BEAM QUALITY IN MAMMOGRAPHY

[75] Inventor: Benjamin M. Galkin, Cherry Hill, N.J.

[73] Assignee: Thomas Jefferson University, Philadelphia, Pa.

[ * ] Notice: The term of this patent shall not extend beyond the expiration date of Pat. No. 5,276,726.

[21] Appl. No.: 345,162

[22] Filed: Nov. 28, 1994

Related U.S. Application Data

[60] Continuation-in-part of Ser. No. 101,950, Aug. 4, 1993, Pat. No. 5,406,612, which is a division of Ser. No. 787,849, Nov. 5, 1991, Pat. No. 5,276,726, which is a continuation-in-part of Ser. No. 441,567, Nov. 24, 1989, Pat. No. 5,063,583.

[51] Int. Cl.$^6$ ................................................. G01D 18/00
[52] U.S. Cl. ................................................. 378/207
[58] Field of Search .............................. 378/207, 204, 378/162, 163, 165, 166, 169, 182

[56] References Cited

U.S. PATENT DOCUMENTS

| | | | |
|---|---|---|---|
| 1,973,906 | 9/1934 | Levene et al. | 250/34 |
| 2,505,562 | 12/1948 | Meschan et al. | 250/67 |
| 3,864,038 | 2/1975 | Palazzolo | 355/114 |
| 3,959,657 | 5/1976 | Katz et al. | 250/476 |

(List continued on next page.)

FOREIGN PATENT DOCUMENTS 2104252  8/1971  Germany.

OTHER PUBLICATIONS

Gray et al., "Quality Control in Diagnostic Imaging, A Quality Control Cookbook", University Park Press, pp. 45–47, 1983.

(List continued on next page.)

*Primary Examiner*—Don Wong
*Attorney, Agent, or Firm*—Woodcock Washburn Kurtz Mackiewicz & Norris

[57] ABSTRACT

Methods and apparatus for correcting the effect on image quality of a film processor which develops a radiographic image of a structure of interest on a film having an emulsion is disclosed. Such methods and apparatus include shielding a first portion of the film along one edge from the x-ray energy used for imaging the structure of interest and impressing a first calibrated test pattern on the first portion of the film. The first pattern includes a first calibrated graded stepwise density pattern having density positions. The density pattern is produced by visible light. A first plurality of symbols is located adjacent the first pattern, wherein each symbol indicates the magnitude of one of the density positions. A control film of similar emulsion as the emulsion of the image film is provided and impressed with a second calibrated test pattern along one edge. The second pattern includes a second calibrated graded stepwise density pattern having density positions, which pattern was also produced by visible light. A second plurality of symbols is located adjacent the second pattern, wherein each symbol indicates the magnitude of one of the density positions. The intensity and spectrum of the visible light used for impressing the first and second patterns is adjustable. The film is processed in a film processor to develop the first pattern and the radiographic image of the structure of interest. The control film is processed to develop the second pattern. The performance of the film processor used to develop the film is measured by comparing and noting the symbols associated with those density positions between the first and second patterns which match. Physical parameters of selected portions of the developed image of the structure of interest are measured, such parameters define image quality. These parameters are corrected for the effect of film processor performance by adjusting the values of the measured physical parameters according to the optical density values at the match positions of the first and second patterns.

1 Claim, 12 Drawing Sheets

U.S. PATENT DOCUMENTS

| | | | |
|---|---|---|---|
| 4,001,592 | 1/1977 | Katz et al. | 250/476 |
| 4,095,111 | 6/1978 | Katz et al. | 250/476 |
| 4,446,365 | 5/1984 | Ong et al. | 250/213 |
| 4,521,808 | 6/1985 | Ong et al. | 358/111 |
| 4,539,591 | 9/1985 | Zermeno et al. | 358/335 |
| 4,718,757 | 1/1988 | Edwards | 354/76 |
| 4,763,002 | 8/1988 | Zermeno et al. | 250/370.01 |
| 4,764,948 | 8/1988 | Hurwitz | 378/165 |
| 4,788,707 | 11/1988 | Malamud et al. | 378/207 |
| 4,860,330 | 8/1989 | Strommer et al. | 378/162 |
| 5,063,583 | 11/1991 | Galkin | 378/207 |
| 5,195,123 | 3/1993 | Clement | 378/162 |
| 5,276,726 | 1/1994 | Galkin | 378/207 |

OTHER PUBLICATIONS

Hendrick, R., "Standardization of Image Quality and Radiation Dose in Mammography", *Radiology* 1990, 174(3), pp. 648–654.

Hendrick, R., "Quality Control in Mammography", *Current Opinion in Radiology* 1989, 1, pp. 203–211.

Herz, "The Photographic Action of Ionizing Radiations. Fundamentals of Radiography", John Wiley & Sons, pp. 100–105, 303, 1969.

X–Rite®383 Operation Manual, Single Sided Exposure Process Control Sensitometer, pp. 9–12.

Herz, "The Photographic Action of Ionizing Radiations", John Wiley & Sons, pp. 275–276, 1969.

Newitt, "Cameras Optimized for Analysis and Measuring", *Advanced Imaging* Jun. 1990, pp. 53–54.

SCHEMATIC OF MAMMOGRAPHY BEAM QUALITY PHANTOM $\mu$ = TOTAL LINEAR ABSORPTION COEFFICIENT $\mu_A \neq \mu_B \neq \mu_C$

NON-UNIFORM THICKNESS

METHOD OF AND APPARATUS FOR STANDARDIZING AND MONITORING BEAM QUALITY IN MAMMOGRAPHY

RELATED APPLICATIONS

The present application is a continuation in part of application Ser. No. 08/101,950 filed on Aug. 4, 1993, now U.S. Pat. No. 5,406,612, which in turn is a divisional application of Ser. No. 07/787,849 filed on Nov. 5, 1991, now U.S. Pat. No. 5,276,726, which in turn was a continuation in part of application Ser. No. 07/441,567 filed on Nov. 24, 1989, now U.S. Pat. No. 5,063,583.

FIELD OF INVENTION

This invention relates generally to the field of radiology, and more specifically to a method and apparatus for standardizing and monitoring beam quality in mammography.

BACKGROUND OF THE INVENTION

Radiographic imaging of the body is well known and extremely useful as a diagnostic tool in the medical arts. Radiographic imaging involves positioning a part of a patient to be imaged denoted as the "structure of interest" under an X-ray tube, exposing the structure of interest to an X-ray beam, and recording the X-ray image on an image receptor. The receptor in most instances is a radiographic film disposed in contact with an intensifying screen. The intensifying screen absorbs x-ray radiation and radiates light in proportion to the radiation absorbed. Light emitted by the intensifying screen exposes the film. The film and screen are kept in tight contact during exposure in a film holder or cassette. After exposing the structure of interest, the film is removed from the cassette, may be labeled with the patient's name and other identifying information, and then developed. The use of radiography to image the human female breast is referred to as mammography.

Mammography is today the most important and accurate method for diagnosing breast disease. The diagnostic value of mammograms is highly dependent on image quality which, in turn, depends upon the interplay of several factors: the size, the angle, and elemental composition of the x-ray target, the energy spectrum of the x-ray beam, the type of imaging system, the image processing system, patient radiation dose, etc. Recent studies by the inventor and by others have shown that there is a wide variation in the quality of mammograms being produced at breast imaging facilities in the United States.

Because of the importance of good image quality in mammography a number of regulatory agencies and professional groups have recommended that mammography facilities have an ongoing quality assurance program. One of these professional groups initiated a voluntary accreditation program for mammography centers in 1987. In order to become accredited a mammography facility must, among other things, submit a radiographic image of a prescribed phantom which contains artifacts that simulate breast calcifications, tumors and fibers. Image quality is determined subjectively, i.e., by visual assessment of a known phantom image having a number of known artifacts.

It is well known in the field of radiology to utilize an inanimate object in place of a patient in conducting serial x-ray exposures for calibration or similar purposes. Such an object is called a phantom and in mammography the object is called a breast phantom. Breast phantoms are composed of materials, for example, certain plastics and wax, that simulate the x-ray absorptive characteristics of a human female breast. Small discrete objects are incorporated in a phantom to differentially absorb x-rays in a manner similar to that encountered in a clinical situation in order to produce an image on a receptor such an x-ray film. These objects are usually called artifacts. In some phantoms the artifacts are imbedded in a wax plate that fits into the plastic body of the phantom. In others the artifacts are imbedded in the plastic itself. The artifacts are also sometimes configured to simulate the physiological shape and approximate size of important clinical markers such as tumors, fibrils and calcifications. State of the art phantoms usually incorporate nylon fibers of different diameter to simulate fibrils, different size particles of alumina oxide, calcium carbonate, calcium hydroxyappotite, calcium sulfate, etc. to simulate breast calcifications and cross sections of nylon spheres to simulate tumors. These artifacts are positioned in the phantom in an arbitrary but generally reproducible way and nominal specifications regarding size and sometimes thickness are provided by the vendor. The phantom used in the accreditation program consists of a plastic block and a wax insert that contains the artifacts. A radiograph of the insert by itself, that is without plastic block, is provided to the user to demonstrate the location of the artifacts. This image is also intended to demonstrate the maximum number of artifacts that can be visualized in a contact radiograph with essentially no excess scatter. In the accreditation program, the complete breast phantom is radiographed and the scatter helps to reduce the number of artifacts seen. Viewers score image quality on the basis of the number of artifacts seen.

The radiation dose and beam quality used to produce the phantom mammogram is calculated from phantom surface exposure measurements, using solid state detectors, i.e., thermoluminscent dosimetry (TLD). These calculations are typically made by a commercial firm independent of the mammography centers or the accrediting organization, the American College of Radiology.

The diagnostic value of radiographic imaging as described above is dependent on the quality of the radiographic image, which in turn depends on an interplay of several factors. One of the more important of these factors is the process by which the radiographic image is developed. Radiographic images which are made on radiographic films are generally developed in devices called "film processors." Film processors are subject to many variations which are functions of the kind of film processor used to develop the film, the age and quality of the chemicals in the film processor which develop the film, the duration of time the film is processed, and the temperature and pH of the chemicals. Since the diagnostic value of a radiographic image is highly dependent upon the quality of the radiographic image, it is imperative that the film processor be well controlled in order to optimally develop the image. It is also important to minimize fluctuation of processor parameters from film to film.

Processor performance, determined by sensitometry/densitometry measurements of the processor used to develop the radiograph, is generally made in-house by the facility seeking accreditation. A separate thirty day record of processor performance is submitted as part of the documentation for accreditation. However, none of these records are directly linked to the phantom image so that the effect of processor performance on the phantom radiograph cannot taken into account in evaluating image quality.

Data from several thousand mammography facilities participating in this program have now been collected. These data continue to show a wide variation in patient dose and image quality, even amongst facilities that are accredited in the aforementioned fashion.

The same professional group has recently introduced a program to re-accredit mammography centers once every three years and to update accreditation on a more frequent basis. The method used for image evaluation and the criteria for re-accreditation remains essentially the same.

The inventor of the subject matter herein claimed and disclosed has recognized a need in the art to improve the current method used to evaluate image quality in mammography. Specifically, a need exists for objective image quality standards rather than the subjective type evaluation now being used in the accreditation program. Such quality standards should be based on physical measurements rather than subjective impressions.

Moreover, processor performance is a critical parameter that needs to be incorporated in any determination of mammographic image quality and the establishment of image quality standards.

A need exists for more frequent independent monitoring of image quality in mammography once in three years, and that this monitoring too, should incorporate a measurement of the effect of film processing on image quality.

As is known by those with skill in the art, an X-ray image of acceptable diagnostic quality generally comprises an image of the structure of interest as a series of gray levels. Examination of the gray level image indicates whether the structure of interest is healthy, or whether the structure of interest may contain certain diseases such as, for example, cancer.

Since the quality of the radiographic image is highly dependent on the film processor, the film processor must be periodically tested to ensure that the images which are produced have a high diagnostic quality. There are several prior methods currently in use to test film processors. One such method involves the use of a "sensitometer" and a "densitometer." A sensitometer is an instrument which impresses a series of graduated exposures on a photographic material. In these sensitometers, a light source of known luminous intensity is displaced at a fixed distance from an exposure plane and emits radiation of known spectral intensity. The surface of the photographic material is positioned to substantially coincide with the exposure plane.

In the sensitometer, an exposure modulating device is located between a film and the light source. If the exposure modulating device is removed, the entire photosensitive material may be uniformly illuminated. However, the purpose of the exposure modulating device is to alter this condition so that various areas of the photosensitive surface are subjected to a series of different exposures, thereby forming a graded density pattern on the photosensitive surface which is developed as a series of gray levels. This density pattern is a function of the type of film and the action of the processor.

After the film is developed by a film processor with the sensitometric graded density gray scale level pattern imposed thereon, a densitometer is used to measure densities created by the exposure modulated device. In this fashion, the graded density pattern, which may be precalibrated in terms of various parameters such as for example, film speed, base and fog, and contrast, can be used to gauge and evaluate the performance of the film processor.

Various other methods and apparatus have been used to test film processors. Examples of these other methods and apparatus are sensitometric film strips which have been pre-exposed and aged, and are then packaged to be sold commercially. These pre-exposed strips are used in conjunction with a readout device. To check the film processor, one of the strips is developed and inserted into the readout device. When the film is withdrawn, the readout device produces a light signal which indicates the temperature and the condition of the chemicals in the processor. No digital readout is provided and no quantitative indications of the condition of the film processor can be determined.

Methods to check film processors by measuring the pH of the chemicals and the operating temperature of the film processor are also known in the art. It has also been known to use "step wedges" to create a graded pattern on radiographic films. These step wedges are generally constructed of an X-ray absorbing material and are used to determine the effect that the X-rays have on the image quality, but not the effect that the film processor has on the image quality.

The aforementioned prior methods for testing a film processor which develops radiographic images do not satisfy long-felt needs in the art for methods and apparatus to test film processors that are quick, efficient and standardized to particular exposures and film types. The recommended frequency for conducting sensitometric and densitometric tests is daily. However, in the realities of the clinical environment, daily testing of film processors is often not completed.

There are many reasons that daily testing is not always accomplished. Chief among these reasons are that special training and equipment are needed, and additional X-ray film is required. As a result, the diagnostic quality of X-ray images is often severely compromised. Poor film processor performance results in degraded radiographic image quality and could ultimately result in failure to detect diseases. This is particularly devastating, for example, in radiographic images of female breasts called "mammograms" where diagnostic features are often subtle, and early detection of breast cancer is often critical to future survival.

The inventor of the subject matter herein claimed and disclosed has recognized a long-felt need in the art to eliminate repeat densitometric readings of test films to monitor the performance of film processors. There are further long-felt needs in the art to minimize the use of extra test films to monitor processor performance, and also to provide the ability to record the effect of processing on the radiographic image for recall during subsequent examinations. A permanent record of processor monitoring for quality assurance and medico-legal needs is also desired in the art.

In sum, breast phantom image quality depends on the interplay of several factors—kVp, mAs, HVL, film/screen system, processing, etc. Current quality control and map test methods are not able to measure the effect on image quality due to changes in one or more of these parameters because of: 1) the limited amount of information that can be elicited from an image of only a breast phantom; and 2) the subjective (visual) method used to assess image quality.

SUMMARY OF THE INVENTION

The advantages of the invention are achieved in methods and apparatus for correcting the effect on image quality of a film processor which develops a radiographic image of a structure of interest on a film having an emulsion. Such methods and apparatus include shielding a first portion of the film along one edge from the x-ray energy used for imaging the structure of interest and impressing a first calibrated test pattern on the first portion of the film. The first pattern includes a first calibrated graded stepwise density pattern having density positions. The density pattern is produced by visible light. A first plurality of symbols is located adjacent the first pattern, wherein each symbol indicates the magnitude of one of the density positions. A control film of similar emulsion as the emulsion of the image film is provided and impressed with a second calibrated test pattern along one edge. The second pattern includes a second calibrated graded stepwise density pattern having density positions, which pattern was also produced by visible light. A second plurality of symbols is located adjacent the second pattern, wherein each symbol indicates the magnitude of one of the density positions. The intensity and spectrum of the visible light used for impressing the first and second patterns is adjustable. The film is processed in a film processor to develop the first pattern and the radiographic image of the structure of interest. The control film is processed to develop the second pattern. The performance of the film processor used to develop the film is measured by comparing and noting the symbols associated with those density positions between the first and second patterns which match. Physical parameters of selected portions of the developed image of the structure of interest are measured, such parameters define image quality. These parameters are corrected for the effect of film processor performance by adjusting the values of the measured physical parameters according to the optical density values at the match positions of the first and second patterns.

BRIEF DESCRIPTION OF THE DRAWINGS

The present invention will be understood, and its numerous objects and advantages will become apparent to those skilled in the art by reference to the following detailed description of the invention when taken in conjunction with the following drawings, in which.

DETAILED DESCRIPTION OF PREFERRED EMBODIMENTS

The present application proposes to solve the above noted problems of the past by supplementing the image of the breast phantom with images of additional objects designed to test different imaging parameters and by supplementing the visual assessment of image quality with optical density measurements of all the recorded images, wherein these measurements are compared against control standards.

To this end, described below are methods and apparatus for testing breast phantom image quality in terms of multi-parameter physical measurements on selected portions of the phantom image and other portions of the imaging film. These methods and apparatus determine the effect of film processing on image quality by coupling a sensitometer pattern to each imaging film. One edge of the film is shielded from x-rays during exposure of the phantom. The shielded area is flashed with a sensitometer. The film is then developed in the regular way.

Densitometric measurements of the developed sensitometer pattern are compared with control measurements to monitor for processor stability and the effect of processing on the phantom image.

Unfortunately, the effect of a change in beam quality on phantom image quality is difficult to determine using present quality control methods, because most automatic exposure control devices are designed to produce a preset film density over the useful kVp range.

The methods and apparatus described below also determine the effect of beam quality on image quality by adding an image of a Mammography Beam Quality Phantom (MBQP) alongside the breast phantom image.

Consider first, sensitometer based methods and apparatus for quality control.

Figure 1A:
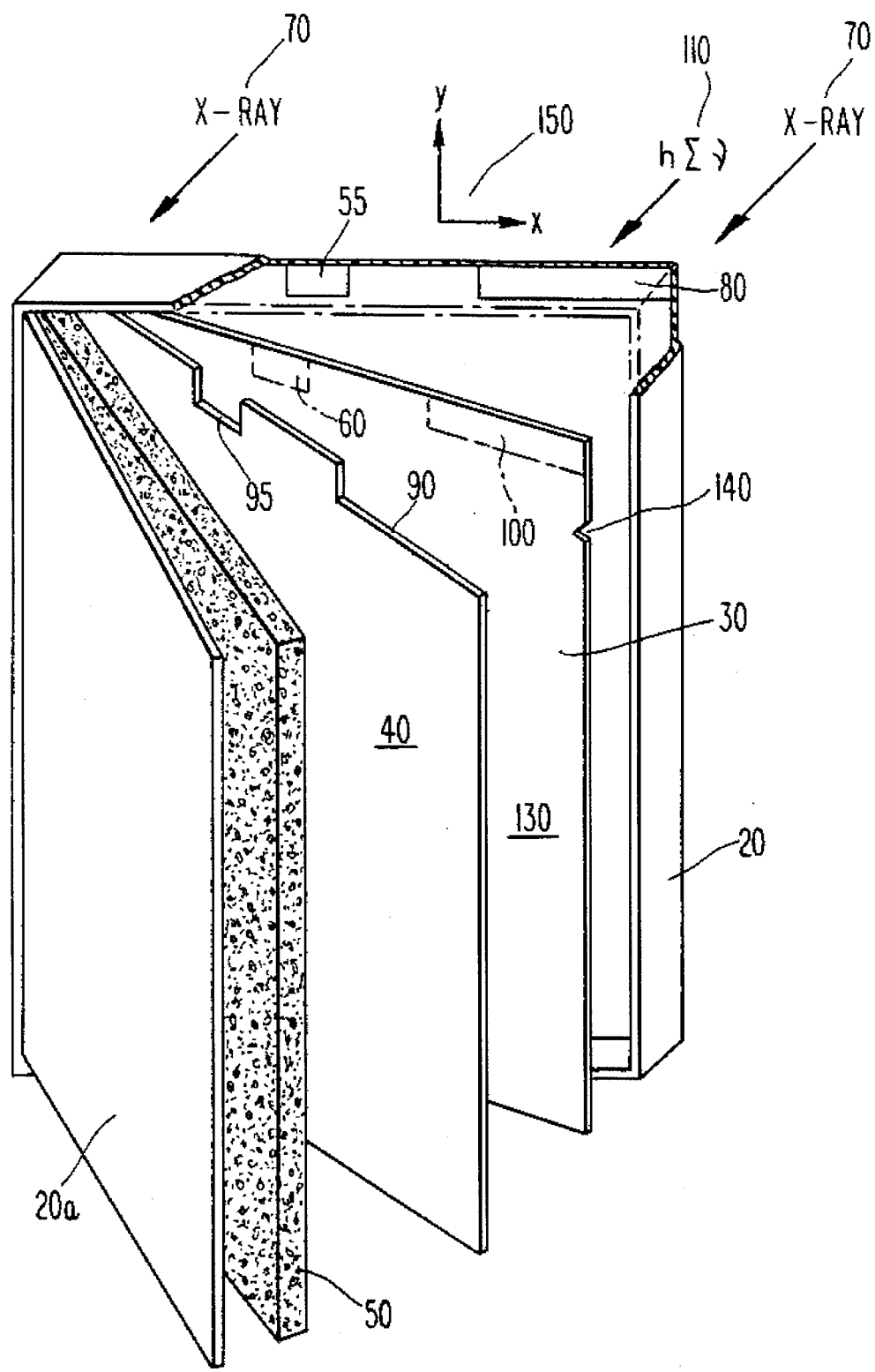
FIGS. 1A and 1B are isometric views of cassettes for holding radiographic films.

Referring now to the drawings wherein like reference numerals refer to like elements, in FIG. 1A a cassette holder having a front cover 20 and back cover 20a provides a housing for the film 30. The film 30 is generally a type of radiographic imaging film. In preferred embodiments, a silver halide emulsion coats a first side of the film 30 and absorbs radiation to form an image of a structure of interest on film 30.

Means for intensifying X-rays 40 is provided to the cassette. Intensifying means 40 is generally a screen that is placed in cooperative relationship with radiographic film 30 to intensify the X-rays, shown at 70, which carry information about the structure of interest. Intensifying screen 40 fluoresces when X-rays 70 impinge on it such that the fluorescent radiation forms an image of the structure of interest on film 30.

In preferred embodiments, film 30 is a single emulsion film for use in mammography. Thus, the structure of interest is a human breast. Since a single emulsion film is used in mammography, only one intensifying screen 40 is provided to the cassette. However, in other radiographic imaging techniques where double emulsion films are typically used, two intensifying screens are provided to the cassette. In describing the invention hereinafter, reference will be made to single emulsion radiographic films for use in mammography wherein the structure of interest is a human breast and the cassettes therefore have a single intensifying screen.

In further preferred embodiments, a pressure pad 50 is placed in the cassette in cooperative relation with intensifying screen 40 so that when the cassette is closed, intensifying screen 40 fits snugly against film 30 during X-ray imaging of the breast. Means 55 for allowing codable information to identify the patient to be impressed on film 30 is integrally formed on front cover 20. Codable means 55 provides for an area 60 on film 30 wherein identifying information of the patient can be impressed on film 30. Codable means 55 blocks X-rays so that coding area 60 is not impressed with a radiographic image during imaging of the breast. Preferably, the identifying information is impressed photographically on coding area 60 after the breast is imaged.

Similarly, means 80 for blocking X-rays 70 is integrally mounted on front side 20 and interfaced with a first portion 100 of film 30 to block X-ray energy from reaching the first portion 100 of film 30. In this fashion after X-rays 70 have irradiated film 30, the silver halide emulsion which exists on the first portion 100 of the film has not been irradiated and remains pristine. Furthermore, intensifying screen 40 does not fluoresce radiation onto first portion 100 since X-rays are blocked from reaching screen 40 in an area corresponding to the first portion 100. Thus, other information may be impressed on the first portion 100 of the film 30, rather than the information about the breast which has been carried by X-rays 70 to a second portion 130 of film 30.

Since the first portion 100 of film 30 and coding area 60 are not to be impressed with radiographic images of the breast, the intensifying screen 40 is cut out at 90 and 95 corresponding to areas on film 30 substantially equal to the area of the first portion 100 and coding area 60 respectively. Since it is desired that no fluorescent energy reaches the first portion 100 of film 30 and area 60, cutouts 90 and 95 in intensifying screen 40 are provided to ensure that no florescent energy reaches the first portion of the film 100 and area 60.

Figure 1B:
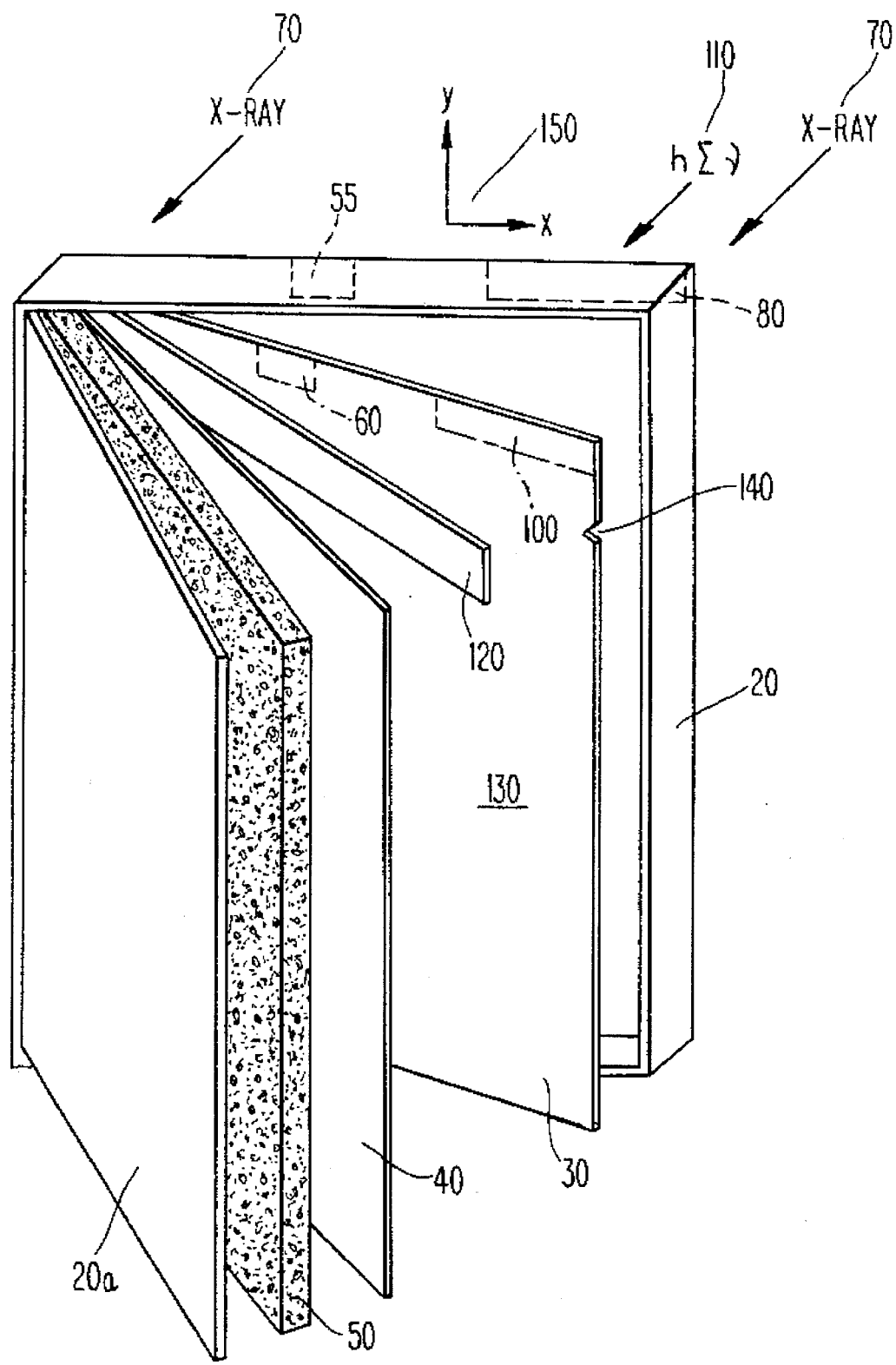

Other means may be provided to the cassette to ensure that area 60 and first portion 100 are not impressed with radiographic images during breast imaging. Referring to FIG. 1B, light blocking means 120 is provided to the cassette disposed between intensifying screen 40 and film 30. Light blocking means 120 is generally a strip of opaque material having approximately the same extent in the X and Y directions as area 60 and first portion 100. Light blocking means 120 prevents florescent energy from reaching area 60 and first portion 100, or more specifically, the space on film 30 corresponding to the area of light blocking means 120.

In yet further preferred embodiments, intensifying screen 40 could simply be made smaller than film 30 so that area 60 and first portion 100 are not illuminated with florescent energy from the screen. Alternatively, an X-ray blocker could be integrally formed in holder 20 to prevent X-rays 70 from reaching areas on screen 40 corresponding to area 60 and first portion 100. An X-ray blocker of this sort preferably comprises a thin sheet of lead which absorbs the X-rays.

The first portion 100 of film 30 is adapted to receive a graded density test pattern which acts as a test means to determine the performance of the film processor that develops the mammogram on second portion 130 of film 30. The graded density pattern is impressed on the first portion 100 of film 30 by a standard sensitometric technique. After the radiographic image has been impressed on second portion 130, film 30 is removed from the cassette in a darkroom so that the graded density pattern can be impressed on first portion 100. Similarly, identifying information for the patient is photographically impressed on coding area 60 after film 30 has been removed from the cassette. During impression of the graded density test pattern on first portion 100, light having a known spectral content, shown generally at 110, irradiates the film on first portion 100. The light 110 is multifrequency, having energy equal to $h\Sigma\upsilon$ signifying radiant energy associated with a range of frequencies. The light 110 is generally emitted from a sensitometer having first been modulated by an exposure modulating device (not shown) and therefore, has a known spectral intensity corresponding to the various frequencies in light 110. A graded density test pattern is thus impressed on film 30 in first portion 100.

In still further preferred embodiments of the cassette provided in accordance with the present invention, the X-ray blocking means 80 and codable means 55 are comprised of a material which absorbs X-rays, thereby preventing the X-rays from reaching intensifying screen 40. Various types of polymer plastics, absorbing foils, or other radiant energy absorbers may thus be used to form X-ray blocking means 80 and codable means 55. Similarly, light blocking means 120 is also constructed of a material which can absorb light comprising multifrequencies.

A graded density test pattern is impressed on the first portion 100 of film 30 by light of known spectral content 110. Thus, film 30 will have essentially two types of useful images impressed thereon. The first image is the standard radiographic image of a structure of interest on the second portion 130 of film 30 called a mammogram. The other image is formed on the first portion 100 of film 30, and is a graded density pattern which is used to test and evaluate the performance of the film processor.

The graded density test pattern is generally a sensitometric image whose development is highly dependent upon the parameters which affect the film processor. Thus, it is possible to use the graded density test pattern to evaluate the film processor's performance independently of other factors that effect the image of the structure of interest, and to ensure that the mammogram formed on the second portion 130 of film 30 is a high quality image that is useful for diagnostic purposes.

It is generally desired to provide means 140 interfaced with film 30 to identify film type. There are many types of radiographic films which can generally be used to form radiographic images. Depending on the type of film used, the film processor will develop the film and produce images whose gray scale is also dependent on film type corresponding to particular radiographic needs.

In yet further preferred embodiments, means 140 for identifying film type is simply a "notch" which is cut out of film 30, and placed in a preferred orientation on film 30. A cartesian coordinate system 150 indicates that notch 140 is oriented along the long edge of film 30. In other preferred embodiments, notch 140 could be oriented along the narrow edge of the film. As is conventional, when film 30 is held in the right hand and notch 140 is in the upper right hand corner, the emulsion side of film 30 faces the individual holding film 30. There may be a single notch, or a series of notches of various shapes cut into film 30 to indicate the particular film type.

Figure 2A:
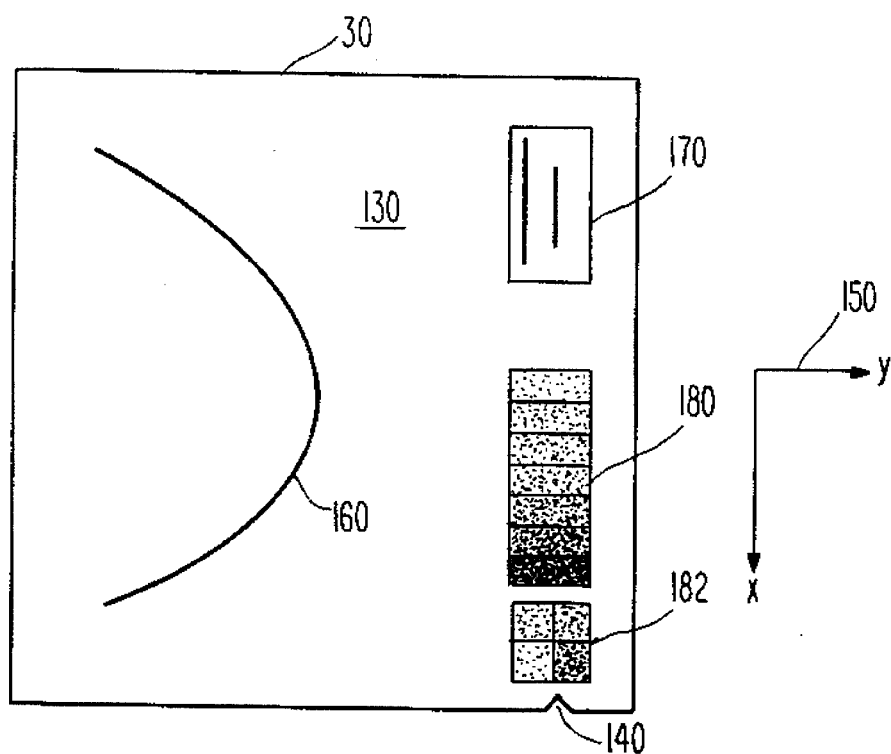
FIGS. 2A, 2B and 2C are schematics of radiographic films in accordance with the present invention.

Referring to FIG. 2A, a radiographic image, herein a mammogram, is shown at 160. As is known by those with skill in the art, female breasts are subject to a particularly devastating form of cancer which, if detected early, may be curable with a high success rate. Thus, high quality mammograms are desired in the radiographic imaging art to allow radiological physicians and professionals to make early and accurate diagnoses of breast cancer.

The film 30 generally comprises an exposable area which is coated with a silver halide emulsion. The exposable area, corresponding to first portion 100, area 60 and second portion 130 in FIGS. 1A and 1B, has impressed thereon various images including mammogram 160, coding area 170 for identifying the patient, and test means 180 and 182 which are generally a graded density test pattern and a contrast pattern that have been sensitometrically produced. In preferred embodiments, coding means 170 may be photographically produced, but it could simply be mechanically attached to the exposable area of film 30. Notch 140 indicates the film type, and is oriented in a preferred direction along an edge of the film.

Figure 2B:
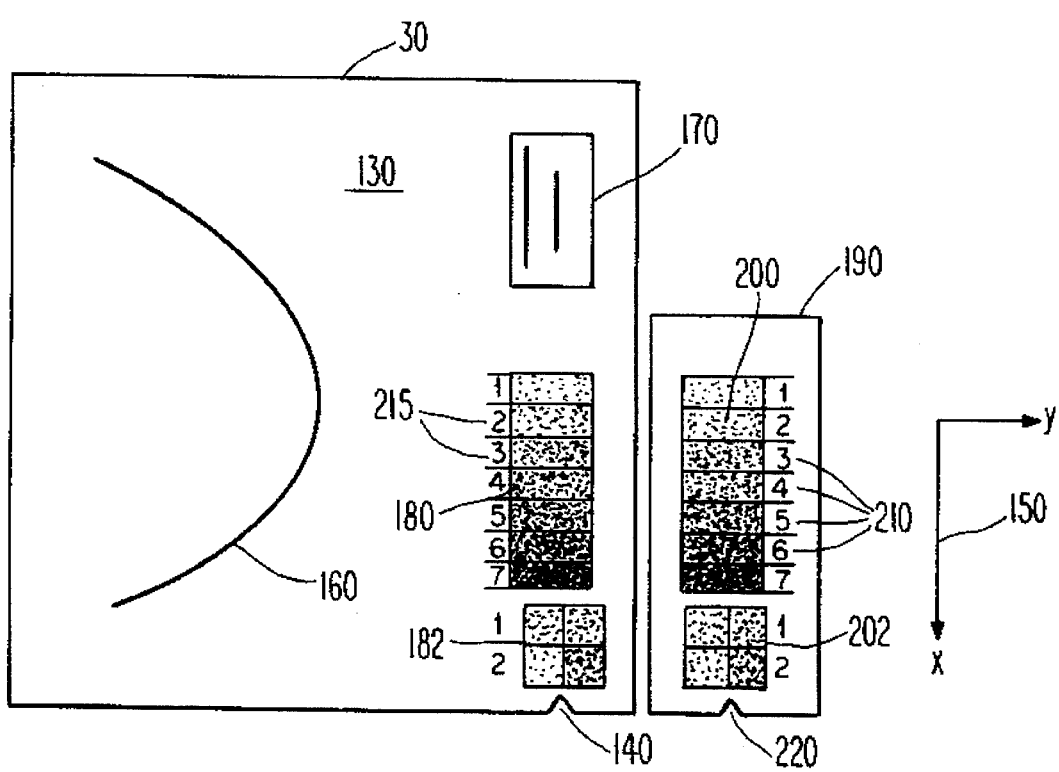
Figure 2C:
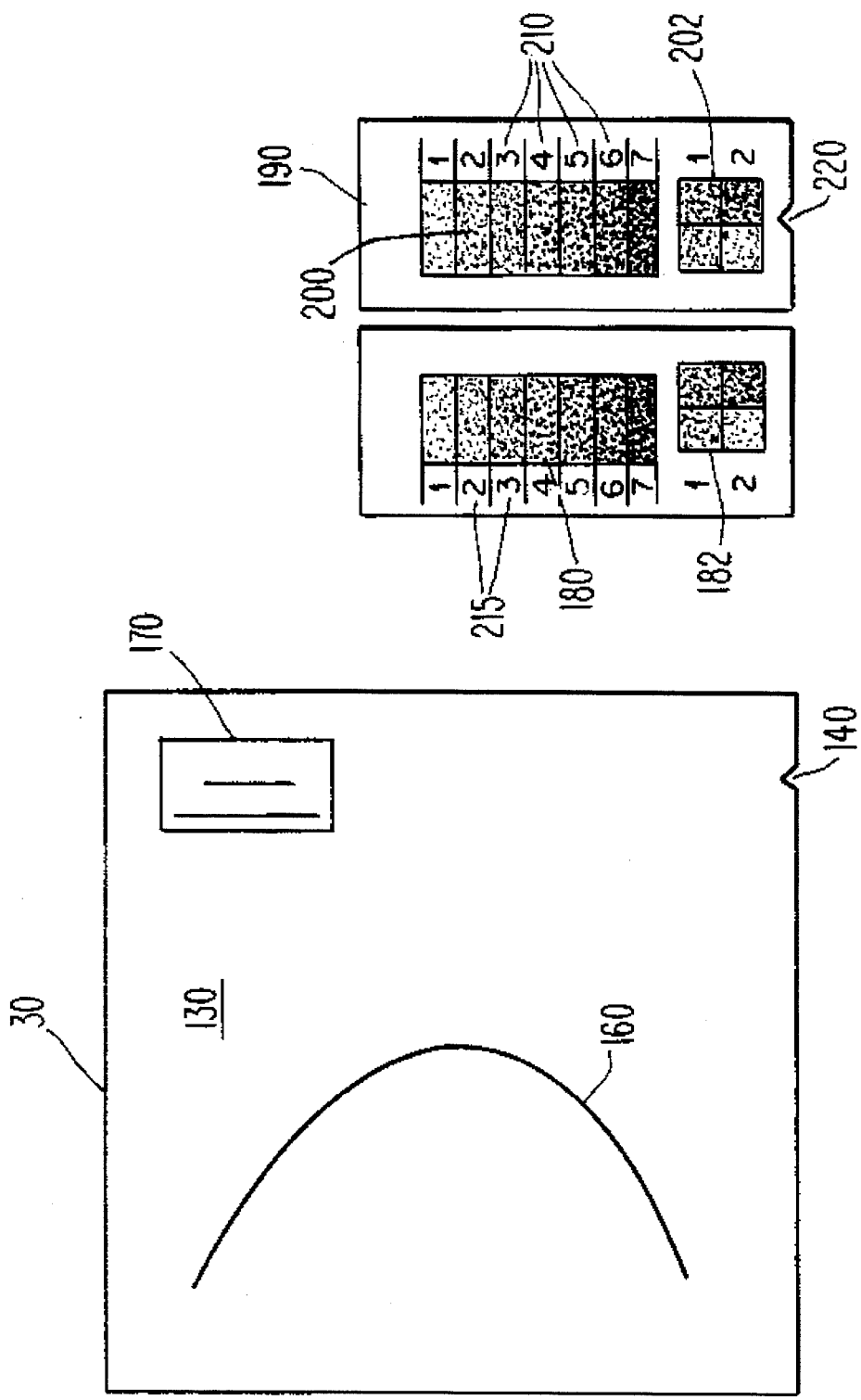

As is illustrated in FIGS. 2A and 2B, graded density test pattern 180 in preferred embodiments is a series of gray levels impressed on film 30. Referring to FIG. 2B, a control film 190 is placed in a proximate position to film 30 so that a control density pattern 200 and a control contrast pattern impressed on control film 190 can be compared to graded density test pattern 180 and contrast pattern 182 impressed on film 30. In preferred embodiments, control density pattern 200 is also a graded density pattern.

In accordance with the present invention, control density pattern 200 impressed on control film 190 is held in position while film 30 having graded density test pattern 180 and mammogram 160 imposed thereon is placed in a proximate position to control film 190 so that graded density test pattern 180 and control density pattern 200 can be visually compared. Variations from accepted norms of graded density test pattern 180 as compared to control pattern 200 may then be visually noted by comparing step markers 210 on control film 190 to step markers 215 on film 30, thereby indicating the quality by which the film processor has developed mammogram 160 on film 30. Step markers 210 and 215 correspond to the various gray levels in control density pattern 200 and graded density test pattern 180, respectively.

Markers 210 provide an indication of what parameters have been measured, for example, film speed, base and fog, and contrast. Control density pattern 200 is calibrated to provide a gray scale indication of a film processor that is considered to be performing optimally in developing radiographic images. By lining up the gray levels on test pattern 180 to the corresponding gray levels on control pattern 200, the difference between step markers 215 and step markers 210 can be noted. Step markers 215 and 210 may be numbers corresponding to gray levels, or generally any type of standardized symbols that provide an indication of the magnitude of the gray levels. The difference between the step markers 215 and 210 after the gray levels on graded density test pattern 180 and control density pattern 200 have been matched provides an indication of how the film processor is performing, and therefore the diagnostic quality of mammogram 160. In a similar manner, the contrast patterns can be compared.

Radiographic films provided in accordance with the present invention eliminate the need for complex, frequent densitometric tests of film processors. Thus radiographic films and control films provided in accordance with the present invention eliminate costly, independent densitometric tests of radiographic films to determine film processor performance, and greatly streamline the testing process for the film processor. No inaccuracies in determining performance of film processors is engendered through the use of methods and apparatus provided in accordance with the present invention because a human eye can detect differences in density of at least 0.05. This is well within the accepted requirements for analyzing sensitometric graded density patterns to determine film processor efficiency and performance.

In accordance with the present invention, notch 220 is physically cut from control film 190 to determine the control film type. By comparing notch 220 with notch 140, the radiologist can ensure that the same type of film which is used in constructing mammogram 160 is used to provide the control density pattern 200.

Methods and apparatus provided in accordance with the present invention are generally useful for both dedicated and non-dedicated film processors. A "dedicated" film processor is one that is used exclusively for developing a single type of radiographic image such as a mammogram. However, most film processors are "non-dedicated" because they are used to develop a number of different kinds of radiographic images including mammograms. Since control film 190 is precalibrated to represent an optimal film processor, it is useful in determining the performance of both-dedicated and non-dedicated film processors. Thus, methods and apparatus for testing both dedicated and non-dedicated film processors provided in accordance with the present invention solve long-felt needs in the art for efficient and cost-effective tests to ensure that mammograms and other radiographic images are of the highest quality for diagnostic purposes. These needs have not been satisfied by methods and apparatus which have existed prior to the invention herein claimed and disclosed.

It is also within the scope of the present invention for the film containing the structure of interest, the first density pattern and the second density pattern to be formed on separate films. In such a situation, each film will have an emulsion, wherein it is preferred for all emulsions to be identical. The density patterns are formed in a manner identical to that described above. It is noted however, that best results can be obtained if the image film and the test film are processed either simultaneously or close in time in the same processor. It may also be desirable to process the control film and the image film simultaneously. It may still further be desirable for the multiple films to have identifying information impressed thereon.

Heretofore, in mammography accreditation programs, such as those presently being conducted, image quality is determined subjectively. A viewer counts and scores image quality on the basis of the number of artifacts visualized in a radiographic image of a standardized phantom. No objective measurements of important image parameters such as contrast, density, resolution, or density gradient are made of the artifacts and no comparison is made against measured physical standards for these variables. The above described embodiments adapt well to resolving the standardization problem.

The standardization problem is resolved by first forming a film and control film as previously described. i.e. with the density and/or contrast patterns impressed thereon. Thereafter such films are processed in a film processor to develop the films. The performance of the film processor is measured by comparing the density positions between the first calibrated test pattern on the film and the second calibrated test pattern on the control film and determining which positions match. If necessary portions of the structure of interest on the film are optically magnified forming a magnified image.

This image is converted to an electrical signal. The physical parameters of the magnified image of the structure of interest are measured from the electrical signal and corrected for the effect of the film processor by adjusting the parameters in relation to the optical density values at the match positions of the first and second calibrated test patterns.

Figure 3:
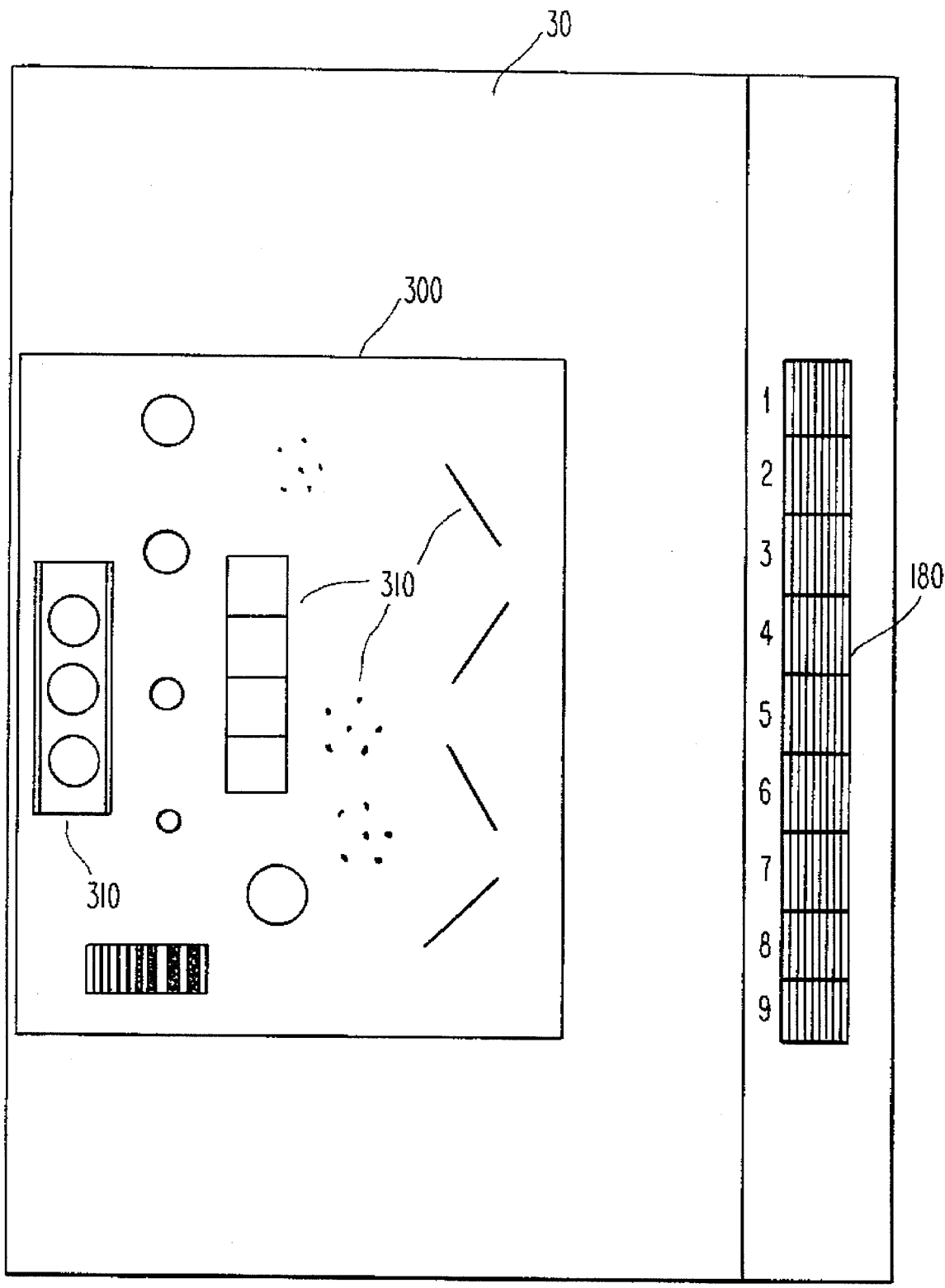
FIG. 3 is an exposed and processed x-ray image containing a number of phantoms for use in the present invention.
Figure 4:
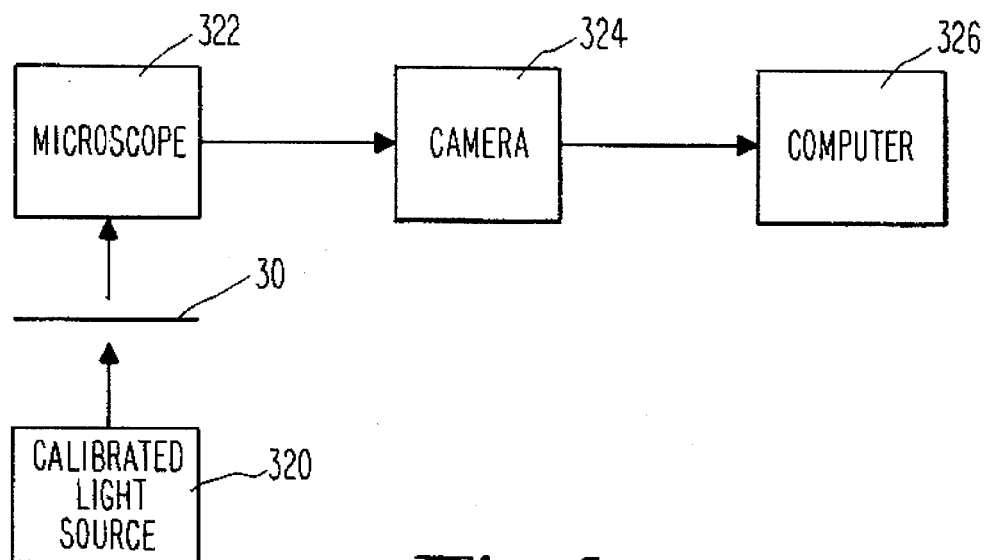
FIG. 4 is a block diagram showing a quality assurance system constructed in accordance with the present invention.
Figure 5:
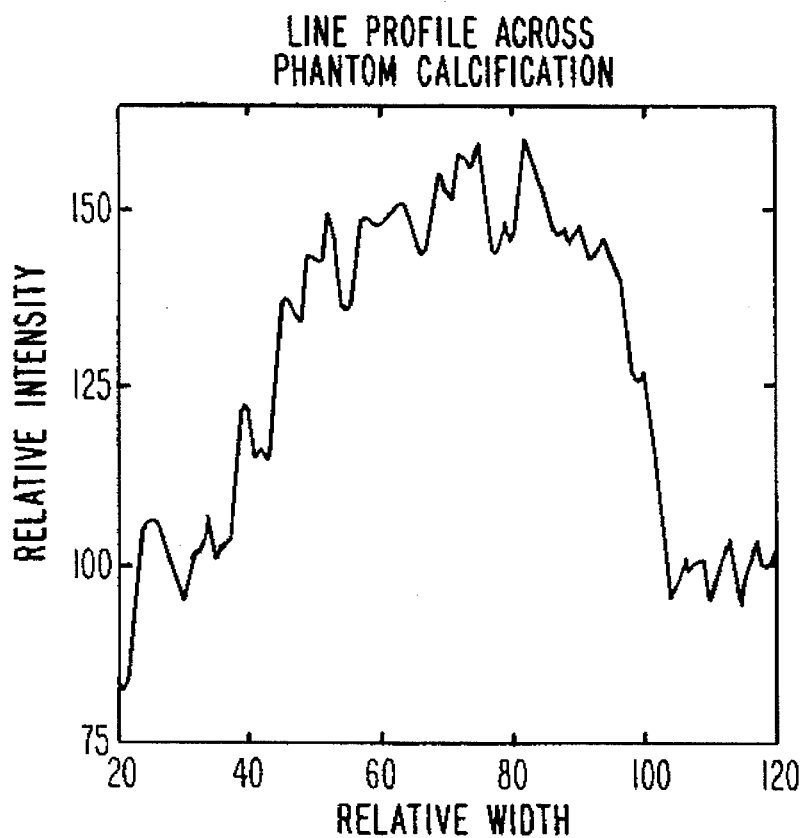
FIG. 5 is a graph showing a line profile across one of the artifacts depicted in FIG. 3.

Such a method can be more clearly understood by reference to FIGS. 3–5. In FIG. 3, a breast phantom 300 has been formed on film 30 together with a graded density pattern 180. As will be appreciated, phantom 300 contains several artifacts 310, which as explained previously are intended to simulate various physiological features of the human breast. One of those artifacts is a calcification. Since such artifacts contain relatively tiny features, that portion of the phantom is magnified. The film also contains images of a 'high contrast and low contrast resolution pattern produced by the x-ray beam. Radiation dose can be measured using separate solid state or film dosimeters exposed while obtaining the radiograph of the phantom. It is noted that FIG. 3 is a schematic representation of a breast phantom and calibrated density pattern, wherein the numbers or symbols represent different density values.

As shown in FIG. 4, film 30 is placed over a calibrated light source. The particular artifact is illuminated by light source 320 which emits light of a known intensity, spectrum and spatial orientation. Such spatial orientation can be determined from the calibration process, wherein a blank is placed over the emitting surface of source 320. Light intensity is then measured so that when an image is placed on the source, corrections can be made for any non-uniformities that are present. It is noted that while a uniform light source is preferred, a calibrated light source can be utilized. Microscope 322, which in the preferred embodiment is a binocular dissecting microscope, receives the light passing through film 30 and magnifies the structure of interest forming a magnified image. It is noted that artifact size can be determined using microscope 322, provided the microscope contains internal measurement features, such as a reticule. It is also noted that for larger artifacts, magnification will not be necessary, however, calibration of the light source is still required. The magnified image is directed in any known manner onto video camera 324, which in the preferred embodiment exhibits a logarithmic response.

Figure 8:
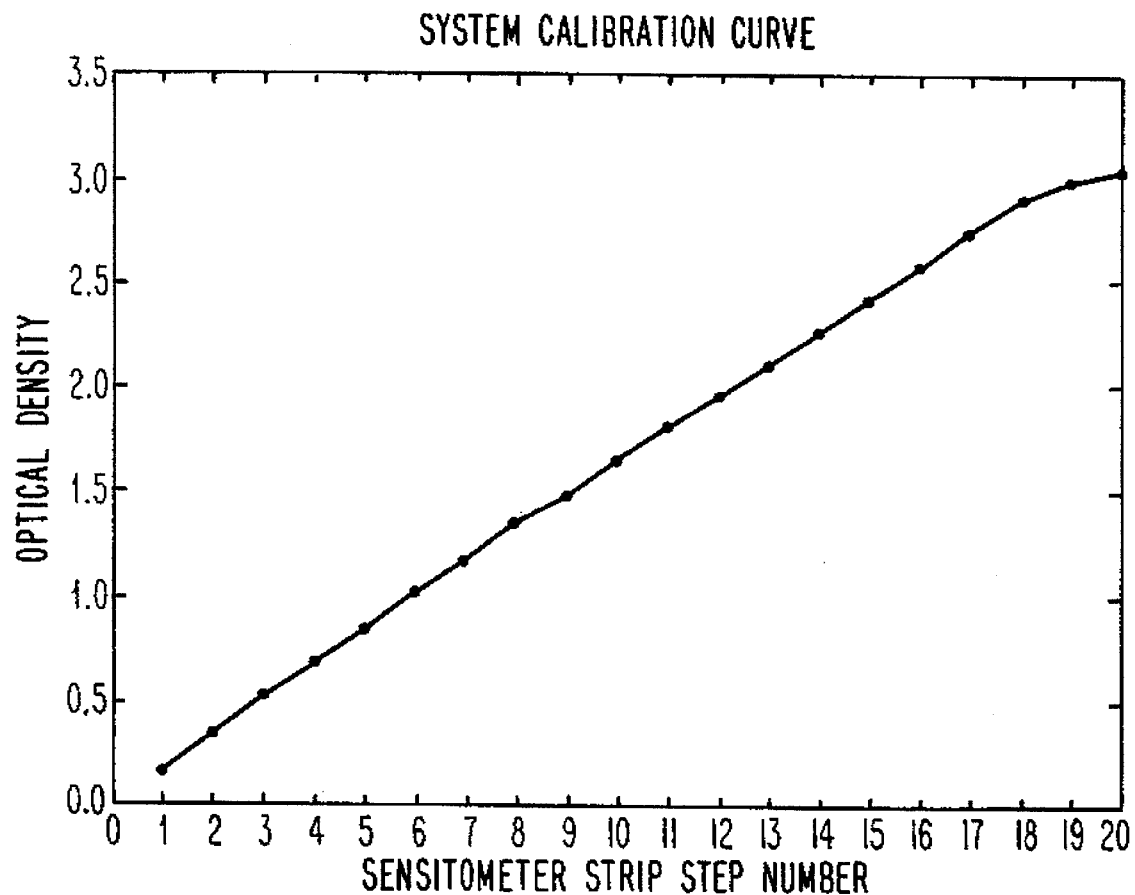
FIG. 8 is a graph of optical density versus sensitometer strip step number.

Camera 324 converts the magnified image into an electrical signal, i.e. digitizes the image, which is provided to computer 326 for storage and/or manipulation. In the preferred embodiment, computer 326 includes a display for displaying the electrical signal. Such a displayed signal is depicted in FIG. 5. From this signal physical parameters can be measured, which parameters are thereafter corrected in relation to a comparison between the density patterns 180 and 200. It is noted that in the preferred embodiment, camera 324 also provides a video monitor. If electronic markers are displayed on the monitor, artifact size can be determined. In the preferred embodiment, camera 324 is an ITM Data Vision Model 250 SOFCAM camera. This camera is preferred because it exhibits a logarithmic response with relation to transmitted light. Such a logarithmic response converts to a linear relationship as shown in FIG. 8.

In the preferred embodiment the graded density patterns are provided with symbols. In such a case, the comparison of the density positions between the test patterns involves noting the symbols associated with those positions on the control film which match.

It is noted that the image quality of a radiographic imaging film can be more accurately evaluated when one utilizes a phantom image, formed in accordance with the above methods or by using apparatus of the present invention, in conjunction with the information relating to the corrections made to the physical parameters to account for the effect of the film processor. Such information can be stored in any known storage device such as an electronic memory, if such information is in the form of an electrical signal or on a hard copy if such information has been printed.

It is also possible to correct for the effect on image quality of a film processor which develops a radiographic image of a structure of interest by taking a film produced in accordance with the above described methods, by measuring the performance of the film processor by comparing and noting the symbols associated with those density positions between the first calibrated test pattern on the film and the second calibrated test pattern on the control film which match, by measuring physical parameters of selected portions of the developed image of the structure of interest, wherein the parameters define image quality and by correcting for the effect of film processor performance on image quality by adjusting the values of the measured physical parameters according to the optical density values at the match positions of the first and second calibrated test patterns.

To obtain the objective data needed to standardize image quality in mammography, the artifacts in the phantom are carefully calibrated according to size, shape, thickness and chemical composition. Sections of the breast phantom image that show the artifacts and other selected portions of the radiograph are measured using the magnification video analysis. Sections of the film containing the image of one or more of the artifacts are optically magnified by a predetermined amount and the magnified images are subjected to video image analysis. The light intensity, light spectra and light uniformity used to illuminate the portion of the film being examined is carefully measured and controlled. The following image parameters are measured: absolute and relative optical density of the images of the artifacts; optical density profiles across the artifacts, line density across high contrast and a low contrast resolution patterns, radiation dose from density measurements of the film, processor performance by density measurements of the graded density pattern.

Figure 6:
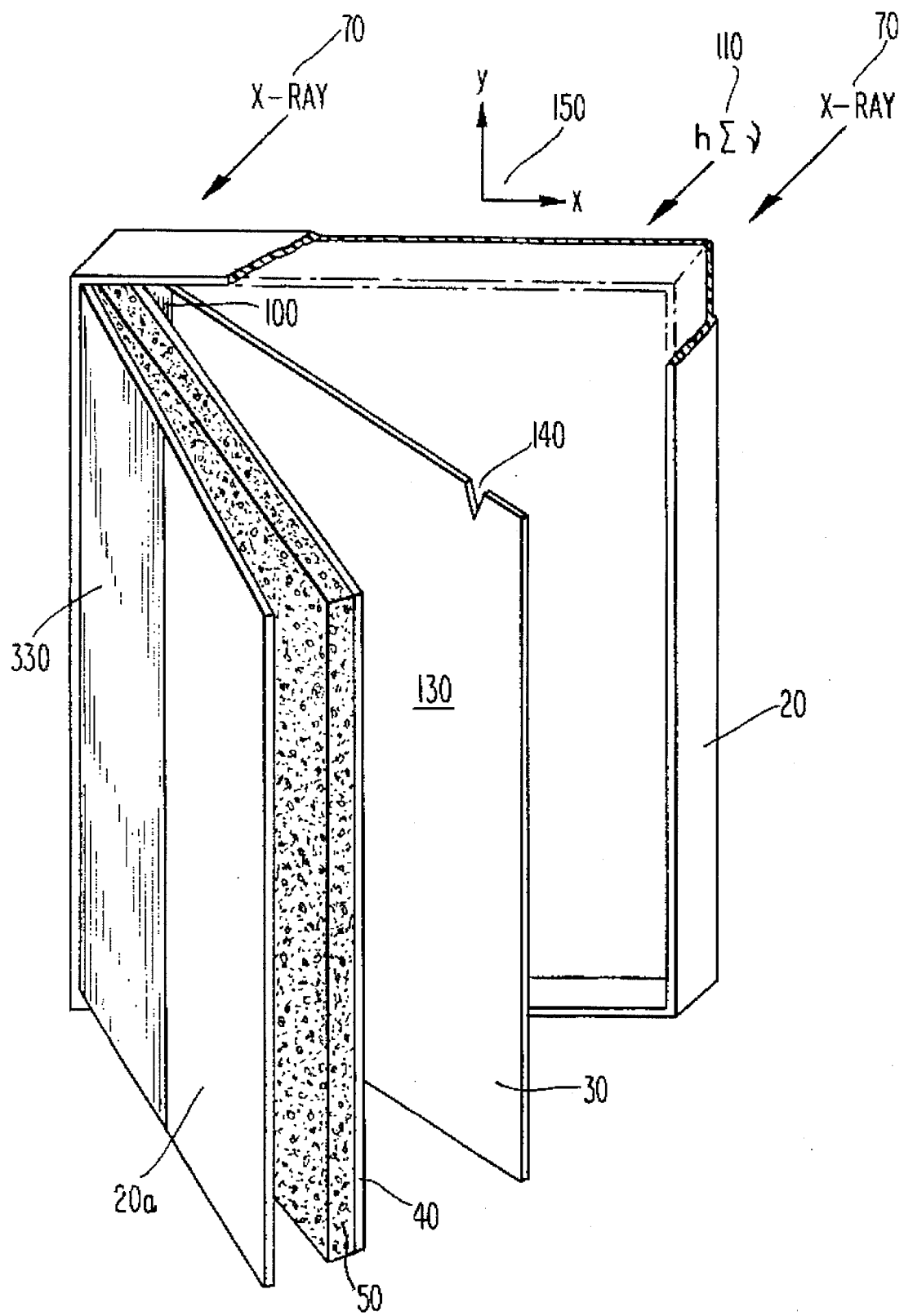
FIG. 6 is an isometric views of cassettes constructed in accordance with the invention for holding radiographic films.

Referring now to FIG. 6, there is shown an alternative cassette, wherein an x-ray impervious shield 330 formed for example from lead is positioned along one edge of cover 20a. Such a shield is used to prevent x-rays from causing the exposure of an edge of film 30. It is preferred to impress the graded density pattern in this area. In the preferred embodiment, shield 330 is formed on the inner surface of cover 20a. However, it is also within the scope of the invention for shield 330 to be formed within cover 20a or on the surface of cover 20a.

Figure 7:
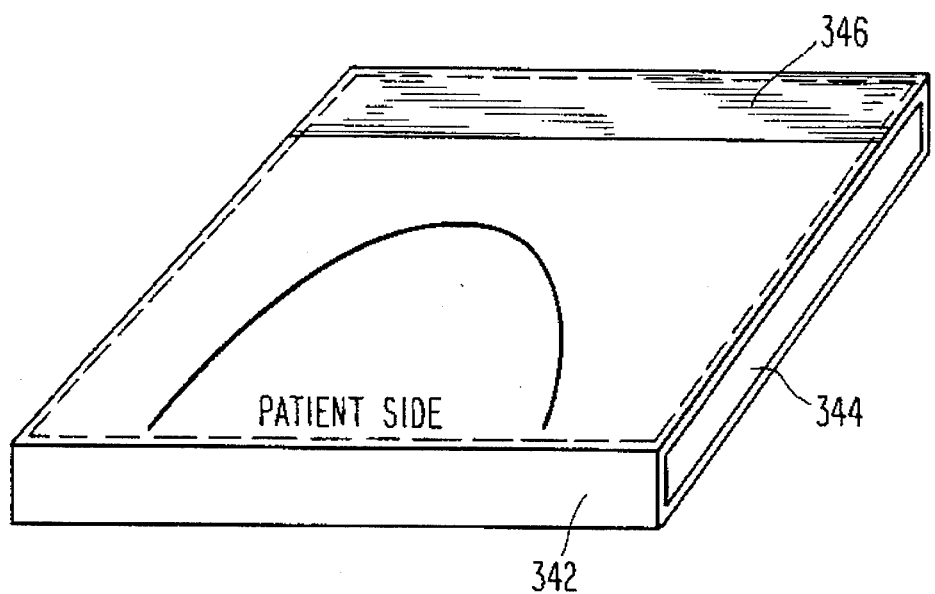
FIG. 7 is an isometric view of a cassette holder constructed in accordance with the invention.

Referring now to FIG. 7, an alternative platform is shown for providing the desired shielding to a portion of film 30 along one edge. In this embodiment there is shown a cassette holder 342. Holder 342 is substantial hollow presenting an opening 344, which is sized for insertion of a cassette such as that shown in FIGS. 1A, 1B and 6. An x-ray impervious shield 346 is formed along one edge of holder 342. When a cassette is inserted, x-rays will be prevented from causing the exposure of film 30 along an edge.

Consider now the use of MBQP methods and apparatus.

Figure 9:
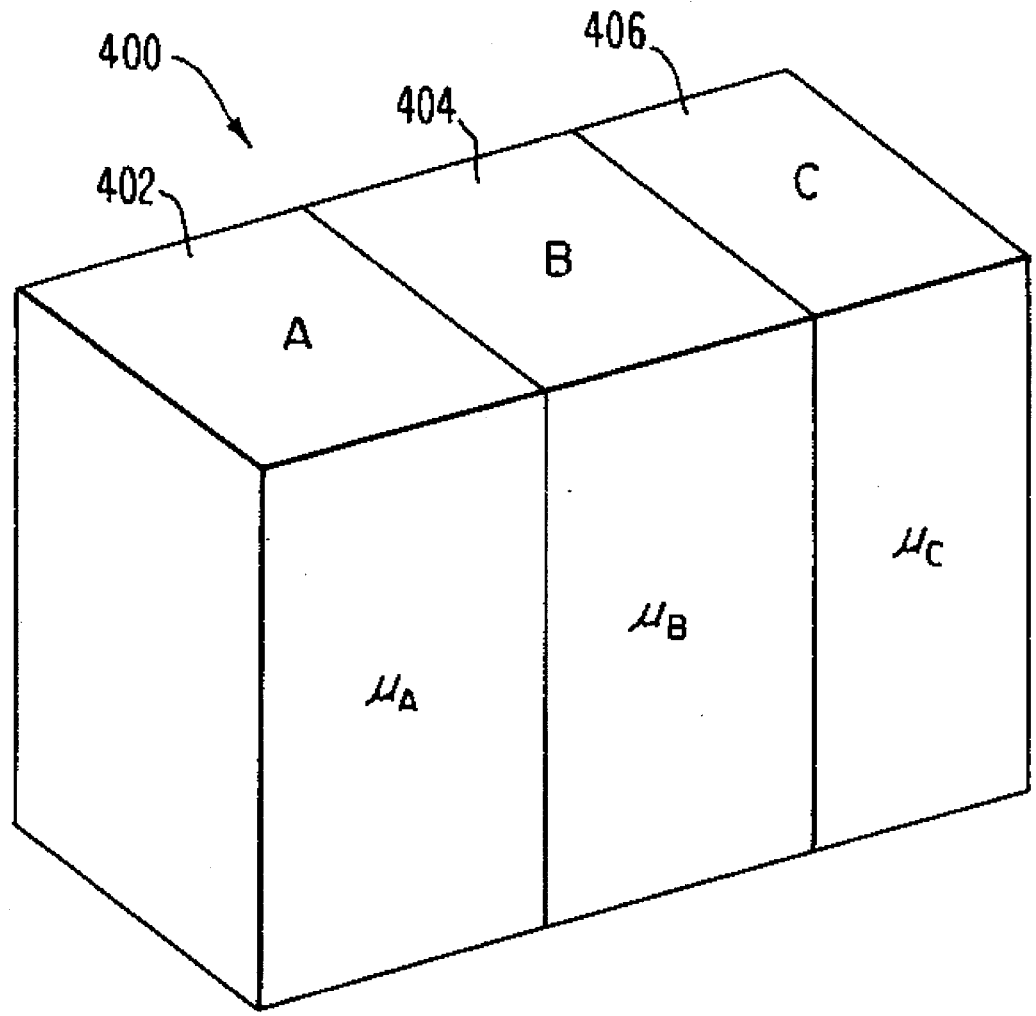
FIG. 9 is a general/schematic perspective view of a mammography beam quality phantom constructed in accordance with the present invention.

The mammography beam quality phantom can be configured to produce a range of optical densities that is suitable for different types of film emulsions and processing. As shown in FIG. 9, an MBQP 400 is shown to include three sections 402, 404 and 406. Each section is shown to have a different absorption coefficient μ. Use of phantom 400 will result in an image being formed on the composite image 410, shown in FIG. 10. Comparison of the beam quality phantom image to a beam quality phantom control image will reveal whether any changes in beam quality exist relative to the beam quality in a control image.

It will be appreciated from the above that when mammography apparatus is calibrated a control image is generated of beam quality phantom 400. Periodically, the mammography apparatus is evaluated by forming the composite image 410 which also includes an image of a beam quality phantom. Comparison of the periodic composite image with the control image of phantom 400 will reveal any deviations in the beam quality, i.e. kVp deviations.

The effect on breast phantom image quality due to changes in focal spot size is also difficult to assess using current quality control methods. As described previously an image of a resolution test pattern is added alongside the breast phantom image as also shown FIG. 10.

Figure 10:
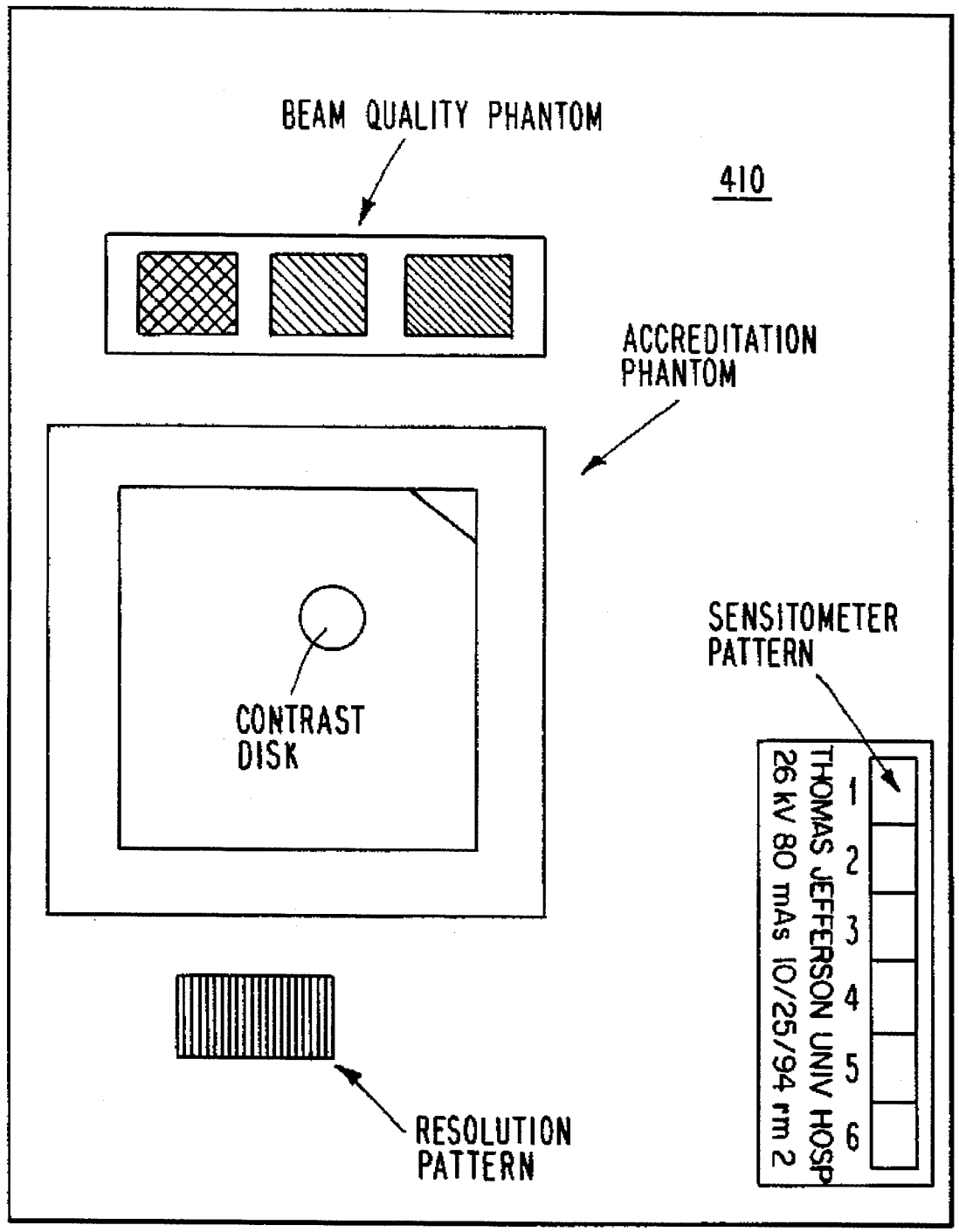
FIG. 10 is a composite image used to determine image quality in accordance with the present invention.

It is noted that in FIG. 10, a small processor monitoring sensitometer pattern is imprinted in the film identification area. Preferably, this pattern is flashed at the same time as the identification information.

Figure 11:
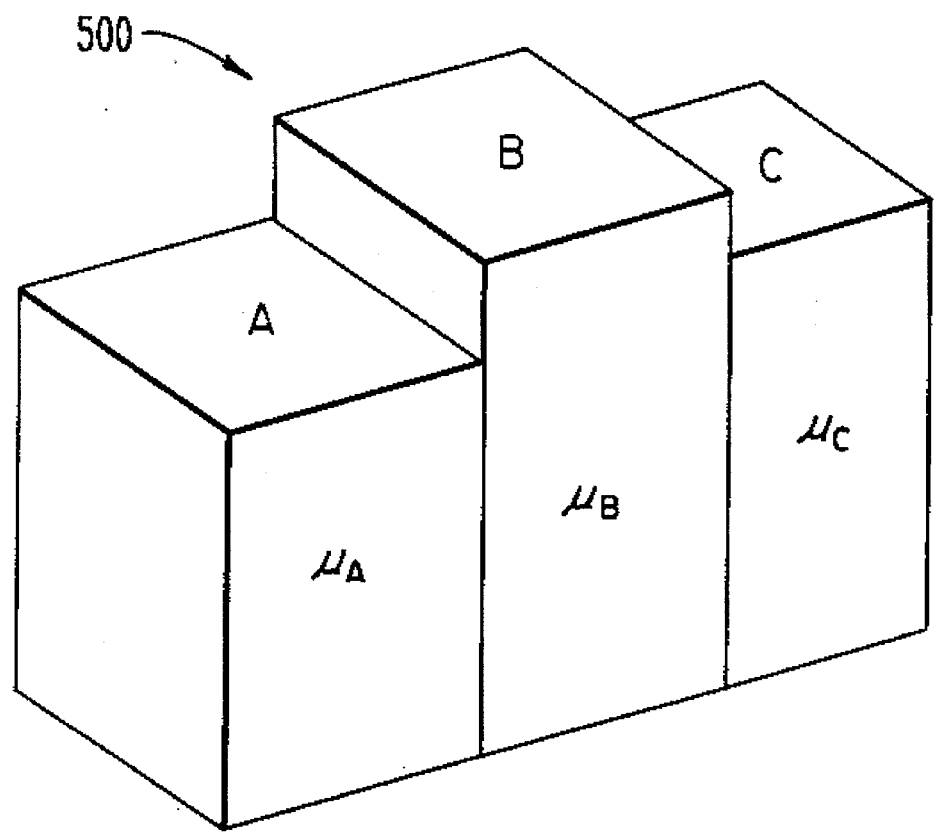
FIG. 11 is a general/schematic perspective view of a non-uniform height mammography beam quality phantom constructed in accordance with the present invention.
Figure 12:
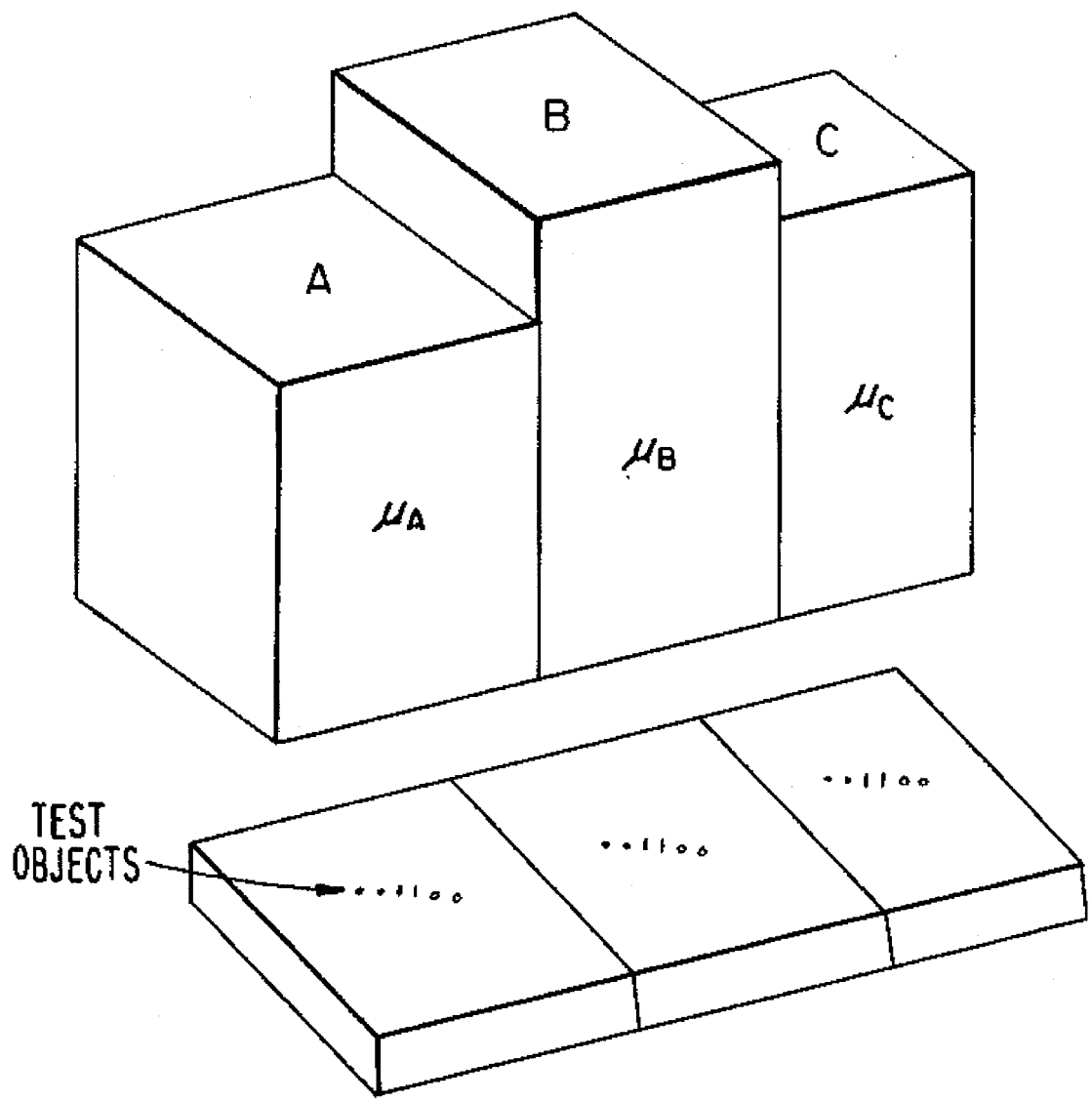
FIG. 12 is a general/schematic perspective view of a non-uniform height mammography beam quality phantom constructed in accordance with the present invention together with test object slabs.

FIG. 11 depicts a beam quality phantom 500, which is similar to phantom 400 except the height of each section is non-uniform. Varying the height of MBQP 500 in this manner results in an image which is more sensitive to variations in the beam quality, i.e. deviations in kVp.

Still further, it may be desirable to place test objects adjacent the MBQP 500.

While the above summary and attached drawings descried the invention as used in film mammography, the invention is also application for xeromammography and other radiographic imaging procedures.

While the invention has been described and illustrated with reference to specific embodiments, those skilled in the art will recognize that modification and variations may be made without departing from the principles of the invention as described herein above and set forth in the following claims.

What is claimed is:

1. A method of correcting measured physical parameters of a radiographic image having a structure of interest for the effect on image quality of a film processor which develops said radiographic image on a film having an emulsion, comprising the steps of:

shielding a first portion of the film along one edge of the film from x-ray energy used for imaging of the structure of interest;

providing a beam quality phantom as said structure of interest;

impressing a first calibrated test pattern on the first portion of the film, said first pattern comprising a first calibrated graded stepwise density pattern having density positions, said density pattern produced by visible light of controlled intensity and spectrum;

providing a control film of similar emulsion as the emulsion of said film;

impressing a second calibrated test pattern along one edge of said control film said second calibrated test pattern comprising a second calibrated graded stepwise density pattern having density positions, said density pattern produced by visible light of controlled intensity and spectrum, wherein the intensity and spectrum of the visible light used for impressing said first calibrated test pattern and second calibrated test pattern are similar;

processing the film in a film processor to develop the first calibrated test pattern on the first portion of the film and the radiographic image of the structure of interest on the second portion of the film;

processing said control film to develop the second calibrated test pattern;

measuring the performance of the film processor used to develop the film by comparing the density positions between the first calibrated test pattern on the film and the second calibrated test pattern on the control film which match;

optically magnifying said structure of interest forming a magnified image, wherein the light source used is corrected for variation in light intensity;

converting said magnified image to an electrical signal;

measuring physical parameters of the magnified image of the structure of interest from said electrical signal; and correcting the measured physical parameters for the effect of the film processor by adjusting said parameters in relation to the optical density values at the match positions of the first and second calibrated test patterns.

* * * * *